(12) United States Patent
Cavallaro

(10) Patent No.: US 9,095,607 B2
(45) Date of Patent: Aug. 4, 2015

(54) GEL FOR TOPICAL APPLICATION OF CLOVE ESSENTIAL OIL WITH BROAD SPECTRUM ANTI-INFLAMMATORY ACTION AND METHOD OF PREPARING SAME

(71) Applicant: Antonino Cavallaro, Miami, FL (US)

(72) Inventor: Antonino Cavallaro, Miami, FL (US)

( * ) Notice: Subject to any disclaimer, the term of this patent is extended or adjusted under 35 U.S.C. 154(b) by 0 days.

(21) Appl. No.: 14/145,785

(22) Filed: Dec. 31, 2013

(65) Prior Publication Data

US 2015/0182578 A1    Jul. 2, 2015

(51) Int. Cl.
*A61K 36/67* (2006.01)
*A61K 36/886* (2006.01)
*A61K 36/61* (2006.01)

(52) U.S. Cl.
CPC ............... *A61K 36/886* (2013.01); *A61K 36/61* (2013.01); *A61K 36/67* (2013.01)

(58) Field of Classification Search
IPC ......... A61K 36/886,36/61, 36/67; A01B 12/006
See application file for complete search history.

(56) References Cited

U.S. PATENT DOCUMENTS

| | | | |
|---|---|---|---|
| 7,273,621 B2 * | 9/2007 | Ozeki et al. | 424/451 |
| 7,736,629 B2 * | 6/2010 | Kamath et al. | 424/58 |
| 8,449,926 B2 * | 5/2013 | Boegli | 424/725 |
| 2007/0207192 A1 * | 9/2007 | Holl et al. | 424/449 |
| 2008/0020018 A1 * | 1/2008 | Moodley et al. | 424/433 |
| 2008/0219938 A1 * | 9/2008 | Grune | 424/59 |
| 2011/0105976 A1 * | 5/2011 | Berlin | 602/48 |
| 2012/0276030 A1 * | 11/2012 | Marthaler et al. | 424/63 |

* cited by examiner

*Primary Examiner* — Patricia A Leith
(74) *Attorney, Agent, or Firm* — Mark Terry

(57) ABSTRACT

A gel for topical application of clove essential oil with broad spectrum anti-inflammatory and analgesic action disclosed containing by weight of the total composition of: 30.0% of deionized water; 0.3% of acrylates/C10-30 alkyl acrylate crosspolymer; 0.1% of glycerin; 0.2% 0.2% of triethanolamine, 0.1% of tocopherol acetate; 0.5% of fragrance; 5% of clove essential oil; 2% of black pepper essential oil; 61.4% of isopropyl alcohol SDA; at least 0.1% of aloe barbadensis leaf extract; 0.2% of parabens mixture; the parabens mixture further comprising of 3% propylparaben, 11% methylparaben, and 30% diazolidinyl; and at least 0.1% (w) of ethylenediamine tetraacetic acid; and the method of preparation of said gel therein.

3 Claims, 11 Drawing Sheets

400

GEL FOR TOPICAL APPLICATION OF CLOVE ESSENTIAL OIL WITH BROAD SPECTRUM ANTI-INFLAMMATORY ACTION AND METHOD OF PREPARING SAME

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The present invention relates generally to anti-inflammatory compositions and, more specifically, to anti-inflammatory and analgesic composition derived from clove essential oil and black pepper essential oil to obtain a topical preparation to alleviate pain and inflammation at site.

BACKGROUND OF THE INVENTION

Anti-inflammatory painkillers are a genre of medicines that can be utilized to alleviate pains, sprains, strains and other common effects of arthritis. They can be consumed orally in the form of tablets, liquids or capsules, injected via needle, or applied to skin in the form of a topical gel or cream. The mechanisms of action of either of these when used as anti-inflammatories is varied.

When applied to skin in the form of a topical preparation, the anti-inflammatory painkillers are sometimes called topical non-steroidal anti-inflammatory drugs (NSAIDs) or just topical anti-inflammatories as a generic term. The NSAIDs are often prescribed as a preliminary treatment for mild to moderate musculoskeletal pain, sprains, strains, and arthritis. High plasma concentrations of oral NSAIDs are required to achieve effective tissue concentrations at the site of pain and inflammation.

In an attempt to find relief of musculoskeletal pain with NSAIDs, topical application NSAID's have been developed to deliver adequate local tissue concentrations with minimal systematic absorption. It has been found that plasma concentrations following topical administration of NSAIDs gels are far lower than levels found after oral administration.

NSAIDs work in the same way as oral anti-inflammatory painkillers, in which the oral anti-inflammatories when taken my mouth, work to inhibit or block the effect of chemicals called cyclo-oxygenase (COX) enzymes. COX enzymes typically aid in the production of prostaglandins, some of which assist in the production of pain and inflammation at site. A reduction in prostaglandin production means lesser pain and inflammation. NSAIDs specifically work only on the area that the topical gel has been applied to rather than the entire body like their oral painkiller counterparts. When topically applied, the NSAIDs are absorbed into the skin of the user and move deeper into the areas of the body like the muscle itself, where there is pain and inflammation exists at site. Using NSAIDs in the form of topical preparation can mean that the total amount of anti-inflammatory in the user's body is very low. This could also mean that that the user is less likely to encounter any potential side-effects due to such use.

However, the effectiveness of topical NSAIDs for the treatment of acute back pain or chronic conditions including chronic back pain is still unknown. Several systematic reviews report trials of poor quality with most trial lengths lasting less than four weeks and demonstrating inconclusive results. Trials comparing oral NSAIDs and their topical equivalents show conflicting results with regards to efficacy. There is insufficient data to perform any thorough meta-analysis. Furthermore, there are not many published results about the effects of NSAIDs in patient populations commonly seen in palliative care settings. Research shows no benefit from a topical NSAIDs cream over placebo in the relief of related pain. Given the expense of topical NSAIDs unclear benefit over prolonged time periods and unknown efficacy compared to oral preparations, they are generally not recommended for chronic musculoskeletal pain.

NSAIDs used regularly for sports injuries, painful joints and arthritis are effective to treat inflammation, however they present skin side effects that can become severe in some people. The topical diclofenac gel has presented allergic contact dermatitis, dryness (irritant dermatitis) and scaling. Also the use of topical NSAID gels or creams to treat pain has been reported to cause a photocontact dermatitis. It has been observed that the reaction appears after stopping the application where the skin is exposed to sunlight. It has also been observed that NSAID gels can produce exanthema, itch, morbilliform, rash, photosensitivity, urticaria and angioedema.

On the other hand, while topical steroids have important benefit in reducing inflammation, they also have significant side effects. Most of the side-effects are seen in long-term use, but some may also be seen within days of starting such a therapy. Side effects consist of: 1) skin atrophy, which causes the thinning of the epidermis and changes in the connective tissue of the dermis, wrinkled skin, hypopigmentation and prominence of underlying veins, 2) alteration in immune function, which can inhibit the skin's ability to fight off bacterial or fungal infections, 3) tachyphylaxis, the tolerance the skin develops to the vaso-constrictive action of topical steroids, 4) steroid rosacea, which is redness and pustules as commonly observed in fair skinned people, 5) topical steroid allergy, which has been observed in 4 to 5 percent of people who use topical steroids, 6) stretch marks in areas where the skin touches skin such as groin and armpits, most of which are itchy, permanent and irreversible, 7) immune-suppression, which is caused when topical steroids are used to skin infection of fungal origin causing the user to get a rash that gets redder, itchier and spreads more extensively than a typical fungal infection. As a result, there is a widespread pustular inflammation called tinea incognito.

Therefore, a need exists to overcome the problems with the prior art as discussed above, and particularly for a more efficient way of providing an anti-inflammatory and analgesic composition.

SUMMARY OF THE INVENTION

The present invention is directed to a formulation, where the anti-inflammatory and analgesic activities of clove essential oil and black pepper essential oil are enhanced within a precise proportion of gel matrix to obtain an effective analgesic and anti-inflammatory topical preparation. The topical gel may relieve inflammatory conditions of various origins and pain associated with inflammatory conditions of various origins at the localized area.

The gel for topical application of clove essential oil with broad spectrum anti-inflammatory action comprising of about 30.0% of deionized water; 0.3% of acrylates/C10-30 alkyl acrylate crosspolymer; 0.1% of glycerin; 0.2% 0.2% of triethanolamine, 0.1% of tocopherol acetate; 0.5% of fragrance; 5% of clove essential oil; 2% of black pepper essential oil; 61.4% of isopropyl alcohol SDA; at least 0.1% of aloe barbadensis leaf extract; 0.2% of parabens mixture; the parabens mixture further comprising of 3% propylparaben, 11% methylparaben, and 30% diazolidinyl; and at least 0.1% (w) of ethylenediamine tetraacetic acid as a chelating agent.

In another embodiment of the present invention, the gel for topical application of clove essential oil with broad spectrum anti-inflammatory action provides a method of preparing an anti-inflammatory topical application of clove essential oil. The method includes the steps of sprinkling acrylates/C10-30 alkyl crosspolymer on a surface of deionized water; mixing the acrylates/C10-30 alkyl crosspolymer and the deionized water at a low speed, dissolving isopropyl alcohol SDA in the acrylates/C10-30 alkyl crosspolymer and deionized water and mixing same, adding following ingredients: glycerin, tocopherol acetate, clove essential oil, black pepper essential oil, aloe barbadensis leaf extract, and a parabens mixture comprising propylparaben, methylparaben and diazolidinyl urea, and mixing same, adding triethanolamine; and adding fragrance, and mixing same; wherein aforementioned ingredients are present in said gel in the following proportions: about 30.0 percent by weight of deionized water; about 0.3 percent by weight of acrylates/C10-30 alkyl acrylate crosspolymer; about 0.1 by weight of glycerin; about 0.2 percent by weight of triethanolamine; about 0.1 percent by weight of tocopherol acetate; about 0.5 percent by weight of fragrance; about 5 percent by weight of clove essential oil; about 2 percent by weight of black pepper essential oil; about 61.4 percent by weight of isopropyl alcohol SDA; at least 0.1 percent by weight of aloe barbadensis leaf extract; about 0.2 percent by weight of parabens mixture, the parabens mixture further comprising of about 3 percent by weight of propylparaben, 11 percent by weight of methylparaben and 30 percent by weight of diazolidinyl urea; and at least 0.1 percent by weight of ethylenediamine tetraacetic acid.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims. The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings. Additionally, the left-most digit of a reference number identifies the drawing in which the reference number first appears.

DETAILED DESCRIPTION OF THE INVENTION

Figure 1:
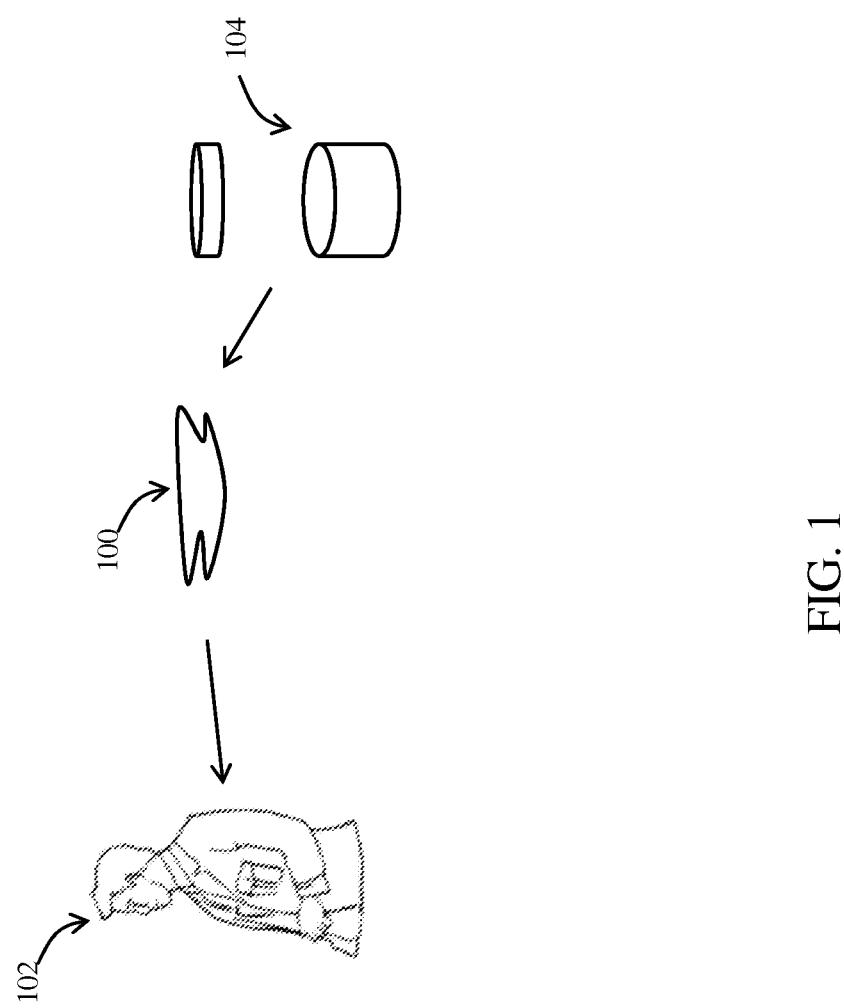
FIG. 1 is a view of the present invention depicting its use.

While embodiments of the invention may be described, modifications, adaptations, and other implementations are possible. For example, substitutions, additions, or modifications may be made to the elements illustrated in the drawings, and the compositions and methods described herein may be modified by substituting, reordering, or adding elements to the disclosed compositions or stages to the disclosed methods. Accordingly, the following detailed description does not limit the invention. Instead, the proper scope of the invention is defined by the appended claims.

The topical gel of clove essential oil and black pepper essential oil of the present invention includes excipients and addition of natural enhancers such as emollient and alcohols that exert their action via a temporary alteration of barrier properties of the skin to enhance the delivery of the clove essential oil flux. The topical gel of clove essential oil and black pepper essential oil of the present invention considers the effect of vehicle to improve the efficacy of delivery of the clove essential oil. The vehicle itself has a cooling emollient and protective action in the formulation.

The topical gel of clove essential oil and black pepper essential oil of the present invention is compatible with the application site. The topical gel of clove essential oil and black pepper essential oil of the present invention further has precise formulation that has been considered according to the results provided by the scientific literature and national regulations. The topical gel of clove essential oil and black pepper essential oil of the present invention has anti-inflammatory properties, has a rapid effect on the affected area, can be used underneath any type of clothing, does not stain, has a pleasant aroma, is germicidal, is not greasy, is simple to apply and can be carried by the user anywhere with ease. Further, in spite of many advantages of gels, a major limitation is the delivery of hydrophobic compounds. The topical gel of clove essential oil and black pepper essential oil of the present invention comprises of emulsion as a base approach so that even the hydrophobic agent such as clove essential oil can be used successfully and delivered through the gel.

The topical gel of clove essential oil and black pepper essential oil also contains eugenol, a major compound of clove essential oil, which has been investigated as a permeation enhancer. This enhances the ability of the topical gel to deliver the clove essential oil flux at a faster rate. The topical gel of clove essential oil and black pepper essential oil also contains major terpens of black pepper essential oil, which has been investigated as an anti-inflammatory. This enhances the ability of the topical gel to deliver the clove essential oil flux at a faster rate. For the foregoing reasons, the present invention comprises of a clove essential oil and black pepper essential oil with broad spectrum anti-inflammatory and analgesic action. The topical gel is easily maneuverable, easily transportable, inexpensive to manufacture, has fewer side-effects, and simple and clinically cost-effective in its application.

The present invention may ease inflammation, muscle pains, strains, and sprains. It can also ease the pain associated with arthritis, iliotibial band syndrome, plantar fasciitis, shin splints, common tendinitis such as lateral epicondylitis, achilles tendinitis, patellar tendinitis, and carpal tunnel syndrome and bursitis. The present invention can be applied at the localized site, thus preventing the harshness of orally consumed NSAIDs, which may have adverse effects on gastrointestinal tracts of the user due to active ingredients such as ibuprofen, diclofenac, felbinac, ketoprofen, or piroxicam that may cause digestive issues.

The present invention is less greasy and can be removed from the skin instantly without any lingering residue and does not negatively impact clothing of the user. The present invention may prevent hepatic first-pass metabolism, used with greater ease in its application, has less fluctuation in drug levels, may achieve efficacy with a lower total daily dose by discontinuation, has the ability to be more "localized" in its delivery, it has improved adherence, and may prevent risks associated with oral or intravenous administration.

FIG. 1 is a view of the present invention depicting its use. FIG. 1 shows that the composition 100 of the present invention may be stored and distributed in a container 104. Subsequently, the composition 100 may be removed from the container 104 and applied to the afflicted site on the patient 102. The composition 100 is structured to be applied topically to the skin in small amounts to cure the patient's affliction, such as inflammation of the skin. A small amount is defined as an amount of gel that easily fits on the finger or hand of the applying individual. A regimen may be used with the composition 100, such as applying the composition 100 to the patient's skin periodically, such as once a day, every morning, for a defined period of time, such as for two weeks.

Embodiments of the present invention provide gel for topical application of clove essential oil with broad spectrum anti-inflammatory action (% weight) comprising of 30.0% of deionized water; 0.3% of acrylates/C10-30 alkyl acrylate crosspolymer; 0.1% of glycerin; 0.2% 0.2% of triethanolamine, 0.1% of tocopherol acetate; 0.5% of fragrance; 5% of clove essential oil; 2% of black pepper essential oil; 61.4% of isopropyl alcohol SDA; at least 0.1% of aloe barbadensis leaf extract; 0.2% of parabens mixture; the parabens mixture further comprising of 3% propylparaben, 11% methylparaben, and 30% diazolidinyl; and at least 0.1% (w) of ethylenediamine tetraacetic acid as a chelating agent as a chelating agent.

As used herein the following terms are intended to have meaning as follows: namely, "anti-inflammatory composition" "composition" and "formulation" meaning pharmaceutical compositions formulated and compounded with a topical gel matrix.

"Gel" or "gel matrix" meaning a colloid that is basically 99% by weight of liquid which is immobilized by surface tension between it and macromolecular network of fibers built from a small amount of a substance gelating material present. Gel or gel matrix may include acrylates/C10-30 alkyl acrylate crosspolymer, and the like.

Figure 2:
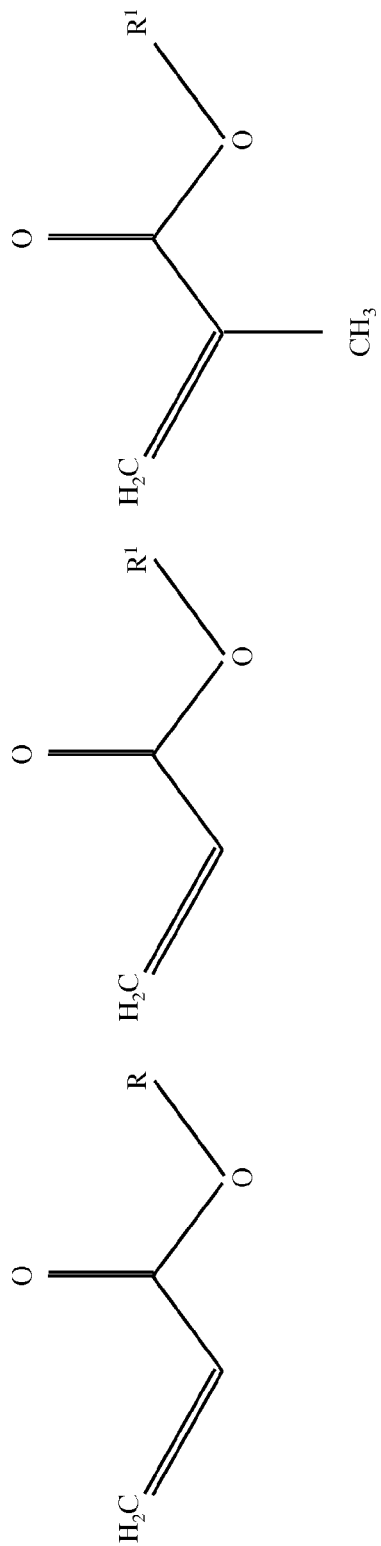
FIG. 2 is a perspective view of the molecular structure of Alkyl Acrylate Crosspolymer.

As used herein, "Alkyl Acrylate Crosspolymer" is intended to mean a copolymer of "C10-30 alkyl acrylate" wherein one or more monomers of acrylic acid, methacrylic acid or one of their simple esters are cross linked with an allyl(2-propenyl) ether of sucrose or an allyl ether of pentaerythritol as represented by the structures shown in FIG. 2.

Alkyl Acrylate Crosspolymer is present in the composition in an amount ranging from 0.3 to 1 percent by weight of the total composition. In a preferred embodiment, R ranges in the amount of 10 to 30 carbon alkyl chain and $R^1$ represents hydrogen or a simple alkali chain. Alkyl Acrylate Crosspolymer is a non-toxic thickening agent that enhances the pleasing feel of the gel and helps it guide smoothly, making it an ideal gel matrix for the active ingredient(s). Alkyl Acrylate Crosspolymer may function as a primary emulsifier in oil-in-water emulsions. Alkyl Acrylate Crosspolymer delivers effective performance across a broad pH range and may have the greatest viscosity efficiency at pH 5.0. Alkyl Acrylate Crosspolymer may function in the composition as a theology modifier.

Figure 3:
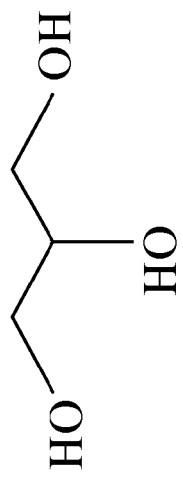
FIG. 3 is a perspective view of the molecular structure of Glycerin.

"Glycerin" meaning "Gliceryn," "Glycerol," "Glycerine," "1,2,3-Propanetriol," "Glyceritol," "Glycyl alcohol," "Trihydroxypropane," "Propanetriol," "Osmoglyn," and "1,2,3-trihydroxypropane" is a trihydroxy sugar alcohol with three hydroxyl groups that are responsible for its solubility in water and its hygroscopic nature and may function in the composition as humectant, improving smoothness, providing lubrication, emollient agent, skin conditioning agent, skin protector, and viscosity decreasing agent as represented by the structure shown in FIG. 3.

"Deionized water" meaning water that is treated with a chelating agent such as tetrasodium ethylenediamine tetraacetic acid or tetrasodium EDTA at a level of 0.05 to 0.10 percent by weight of the total composition. Deionized water prevents the clarity and viscosity from being negatively affected due to carbopol polymers' sensitivity to hard water ions.

"Caprylyl glycol" meaning "1,2-octanediol," "1,2-dihydroxyoctane," "octane-1,2-diol," "1,2-octylene glycol," "1117-86-8," and "(S)-1,2-octanediol" may function as a humectant, skin conditioning agent, bacteriostatic, bactericidal and inhibiting agent of the yeast growth. Caprylyl glycol may also serve as a formulation stabilizer and viscosity regulator.

"Isopropyl myristate" meaning "isopropyl tetradecanoate," "estergel," "promyr," "tetradecanoic acid," "1-methylethyl ester," "bisomel," "isomyst," "kesscomir," and "tegester" is an ester of myristic acid and isopropyl myristate and may function as a binder, skin-conditioning agent and emollient agent.

Figure 10:
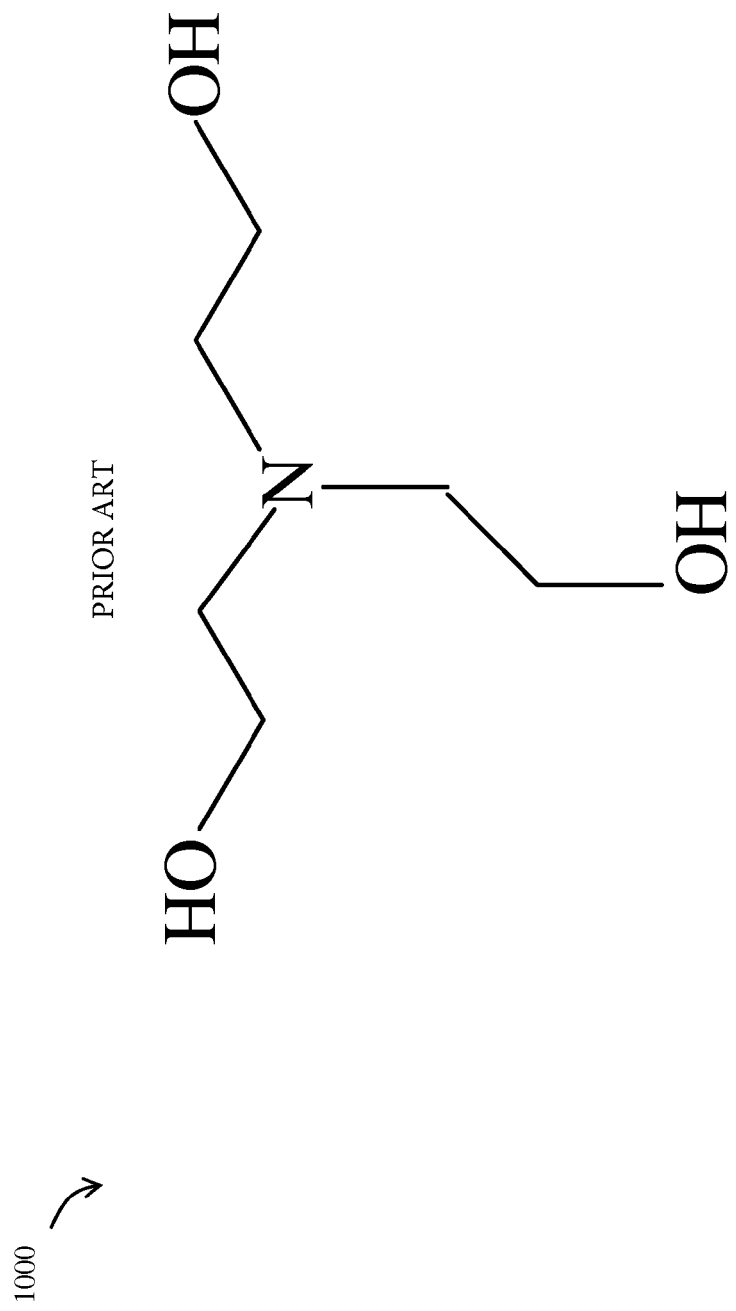
FIG. 10 is a perspective view of the molecular structure of Triethanolamine.
Figure 11:
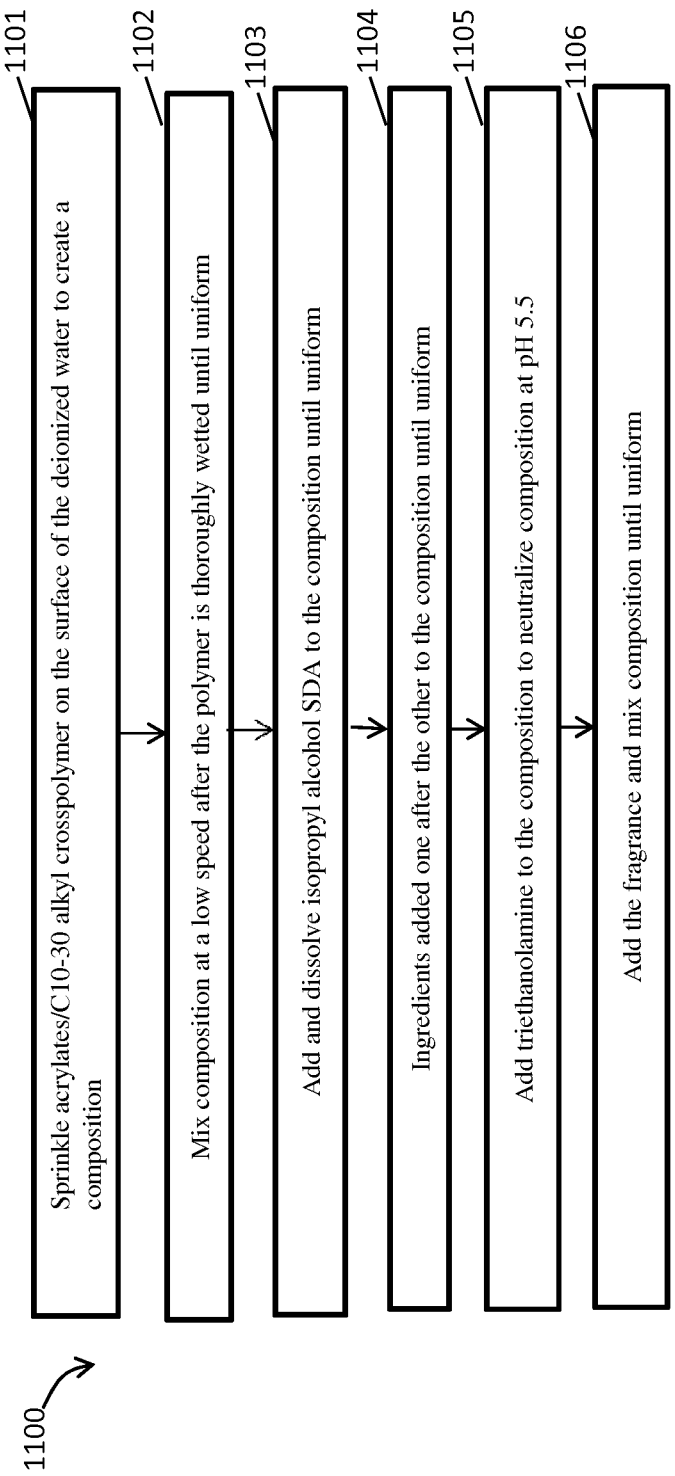
FIG. 11 is a flow chart illustrating the steps of preparing the present invention.

"Triethanolamine" meaning "trolamine," "2,2',2''-Nitrilotriethanol," "daltogen," sterolamide," "tris(2-hydroxyethyl) amine," "triethylolamine," and "trihydroxytriethylamine" may function in the formulation as a thickener and "pH" adjuster, where "pH" is a figure expressing the acidity and alkaline on a logarithmic scale that ranges from 0-14 on which 7 is neutral (less than 7 means acidic and more than 7 means alkaline). Triethanolamine may not exceed 0.2 percent by weight of the total composition as represented by the structure shown in FIG. 10.

Figure 6:
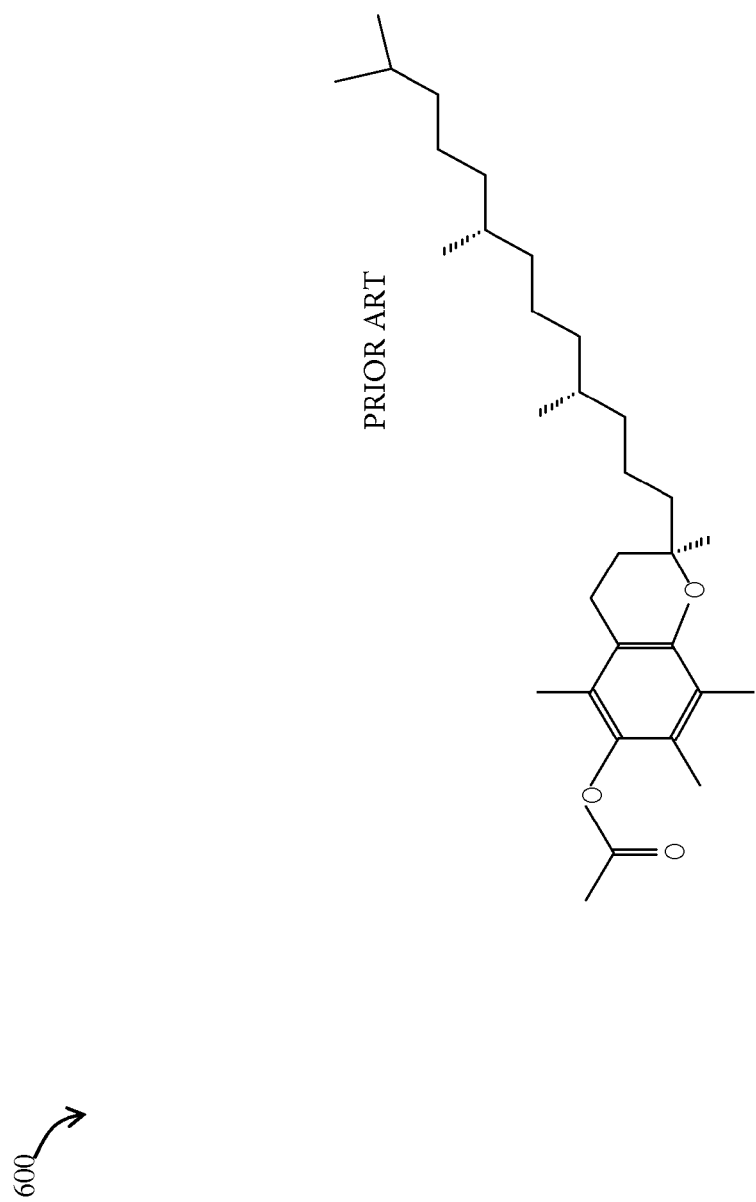
FIG. 6 is a perspective view of the molecular structure of Tocopherol acetate.

"Tocopherol acetate" meaning "tocopheryl acetate," "vitamin E acetate," "DL-alpha-tocopheryl acetate," "ephynal," "syntopherol acetate," and "rovimix E 50SD" is a collective name for a group of closely related lipids that contain substitutions on the 2H-1-benzopyran-6-ol nucleus and a long hydrocarbon chain of isoprenoid units may function in the formulation as an antioxidant and skin conditioning agent, as represented by the following structure shown in FIG. 6. Tocopherol acetate may not exceed 0.1 percent by weight of the total composition.

Figure 4:
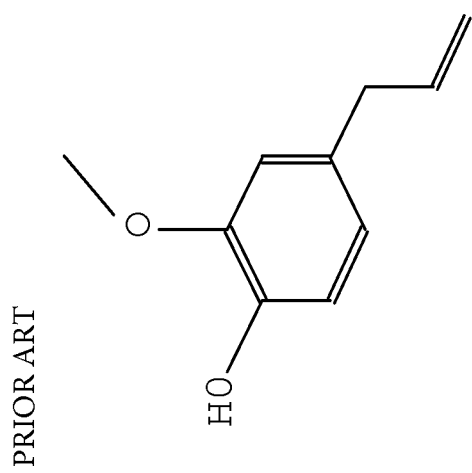
FIG. 4 is a perspective view of the molecular structure of Eugenol, the main component of clove essential oil.

"Clove essential oil" is a clear to pale yellow liquid that has a spicy clove-like aroma and contains eugenol as one of its principal components of clove oil. The composition of clove essential oil may include eugenol in the range of 49 to 87 percent by weight of the total clove essential oil mixture, beta-caryophyllene in the range of 4 to 21 percent by weight of the total clove essential oil mixture and eugenyl acetate in the range of 0.5 to 21 percent by weight of the total clove essential oil mixture. Eugenol is represented by the structure shown in FIG. 4. Smaller amounts of alpha-humulene along with trace amounts of other 25-35 compounds are also present. The clove essential oil may function in the composition as an anti-inflammatory agent. Clove essential oil may not exceed 5 percent by weight of the total composition.

Figure 5:
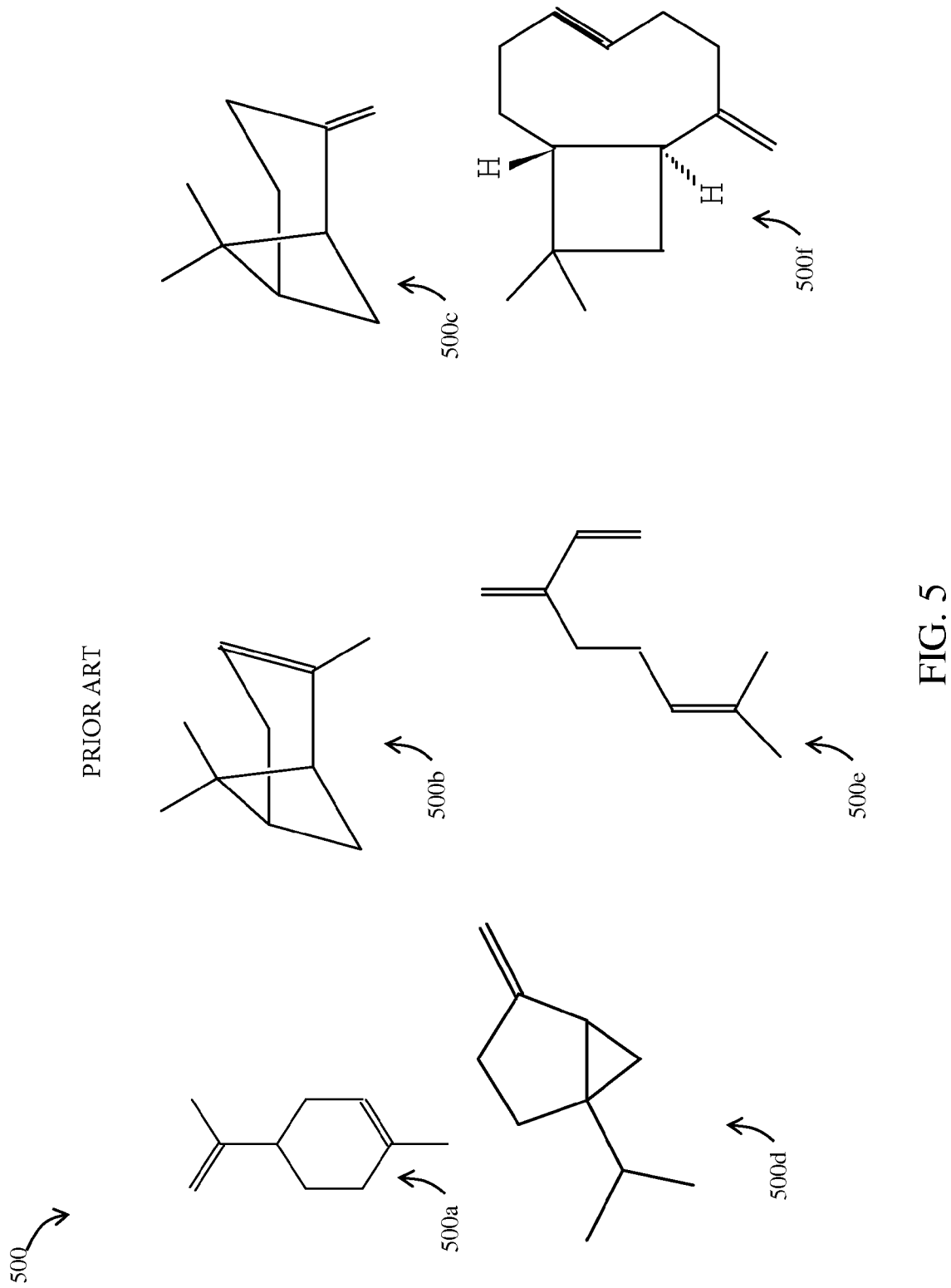
FIG. 5 is a perspective view of the molecular structure of various terpens of black pepper essential oil; 500a is the molecular structure for limonene; 500b is the molecular structure for alpha pinene; 500c is the molecular structure for beta pinene; 500d is the molecular structure for sabinene; 500e is the molecular structure for myrcene; 500f is the molecular structure for beta caryophyllene.

"Black pepper essential oil" is a clear, aromatic liquid that contains the principal components of black pepper oil. FIG. 5 is a perspective view of the molecular structure of various terpens of black pepper essential oil; 500a is the molecular structure for limonene; 500b is the molecular structure for alpha pinene; 500c is the molecular structure for beta pinene; 500d is the molecular structure for sabinene; 500e is the molecular structure for myrcene; 500f is the molecular structure for beta caryophyllene. The black pepper essential oil may function in the composition as an anti-inflammatory agent. Black pepper essential oil may not exceed 2 percent by weight of the total composition.

Black pepper contains about 2.0-2.6% volatile oil and about 6-13% oleoresin. The black pepper essential oil contributes towards the aroma, oleoresin contributes towards the overall taste. Produced by steam distillation from the black peppercorns, the essential oil is water white to pale olive in colour, with a warm, spicy (peppery) and fresh aroma. The black pepper oil constituents are monoterpene hydrocarbons, sesquiterpene hydrocarbons and miscellaneous compounds. Monoterpene hydrocarbons identified in the black pepper essential oil are camphene (from 0.13 to 0.18%), δ-3-carene (from 1.03 to 2.82%), p-cymene (from 0.07 to 9.70%), limonene (from 22 to 31%); myrcene (from 2.30 to 8.40%), cis-ocimene (from 0.30 to 2.84%), α-phellandrene (from 0.2 to 2.32), β-phellandrene (from 0.20 to 0.68%), α-pinene (from 5.9 to 12.8%), β-pinene (from 10.6 to 35.5%), sabinene (from 1.94 to 17.16%), α-terpinene (from 0.39 to 1.13%), γ-terpinene (from 0.01 to 0.49%), terpinolene (from 0.08 to 0.22%), and α-thujene (from 0.73 to 1.59%). Also, there are 43 oxygenated compounds of a monoterpenoid nature have been characterized. The major sesquiterpene hydrocarbon present in pepper oil is β-Caryophyllene ranged from 22 to 28%. Other sesquiterpenes also reported in the essential oil of black pepper are α-cis-bergamotene, α-trans-bergamotene, β-bisabolene, δ- and γ-cadinenes, calamenene, α-copaene, α- and β-cubebenes, ar-curcumene, β- and δ-elemenes, β-farnesene, α-guaiene, α- and γ-humulenes, isocaryophyllene, γ-muurolene, α-santalene, α- and β-selinenes, ledene, sesquisabinene, and zingiberene.

The black pepper essential oil in the formulation of topical delivery system contains a variety of terpenes with proven medicinal activities. The combination of the two essential oils (clove and black pepper) in the formulation of topical delivery system corresponds to a composition which enhances anti-inflammatory and anesthetic properties. Limonene, α-pinene, β-pinene, sabinene, myrcene, and β-caryophyllene are the major components in black pepper essential oil. The other major component of the black pepper essential oil is the sesquiterpene β-Caryophyllene in the order of 22 to 28%. This natural product has shown having anti-inflammatory activity, but with no analgesic properties. Beta-caryophyllene (trans-caryophyllene) and Alpha-humulene inhibit the LPS-induced NF-kB activation and neutrophil migration, although only Alphahumulene had showed the ability to prevent the production of proinflammatory cytokines TNF-α and IL-1b and the in vivo up-regulation of kinin B1 receptors. Moreover, both compounds suppressed the LPS-induced neutrophil recruitment and NFkB activation, without interfering with the activation of mitogen-activated protein (MAP) kinases.

Thus, black pepper essential oil contributes through its anti-inflammatory and anesthetic properties to the formulation of topical clove and black pepper essential oils delivery system with broad spectrum anti-inflammatory. Concentrations of clove and black pepper essential oils in the topical formulation release delivery are not health hazards.

Figure 9:
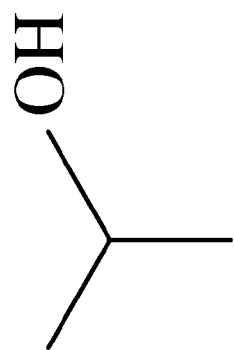
FIG. 9 is a perspective view of the molecular structure of Isopropyl alcohol.

"Isopropyl alcohol" meaning "2-propanol," "isopropanol," "isopropyl alcohol," "propan-2-ol," "sec-propyl alcohol," "2-hydroxypropane," and "dimethylcarbinol" is a widely used ingredient in cosmetics and personal care products and kills and prevents growth of microorganisms. It may function in the formulation to dissolve the clove essential oil and black pepper essential oil, provide cooling effect upon evaporation, decrease thickness, act as a solvent and to prevent growth of microorganisms as represented by the structure shown in FIG. 9. Isopropyl alcohol may not exceed 61.4 percent by weight of the total composition.

Figure 7:
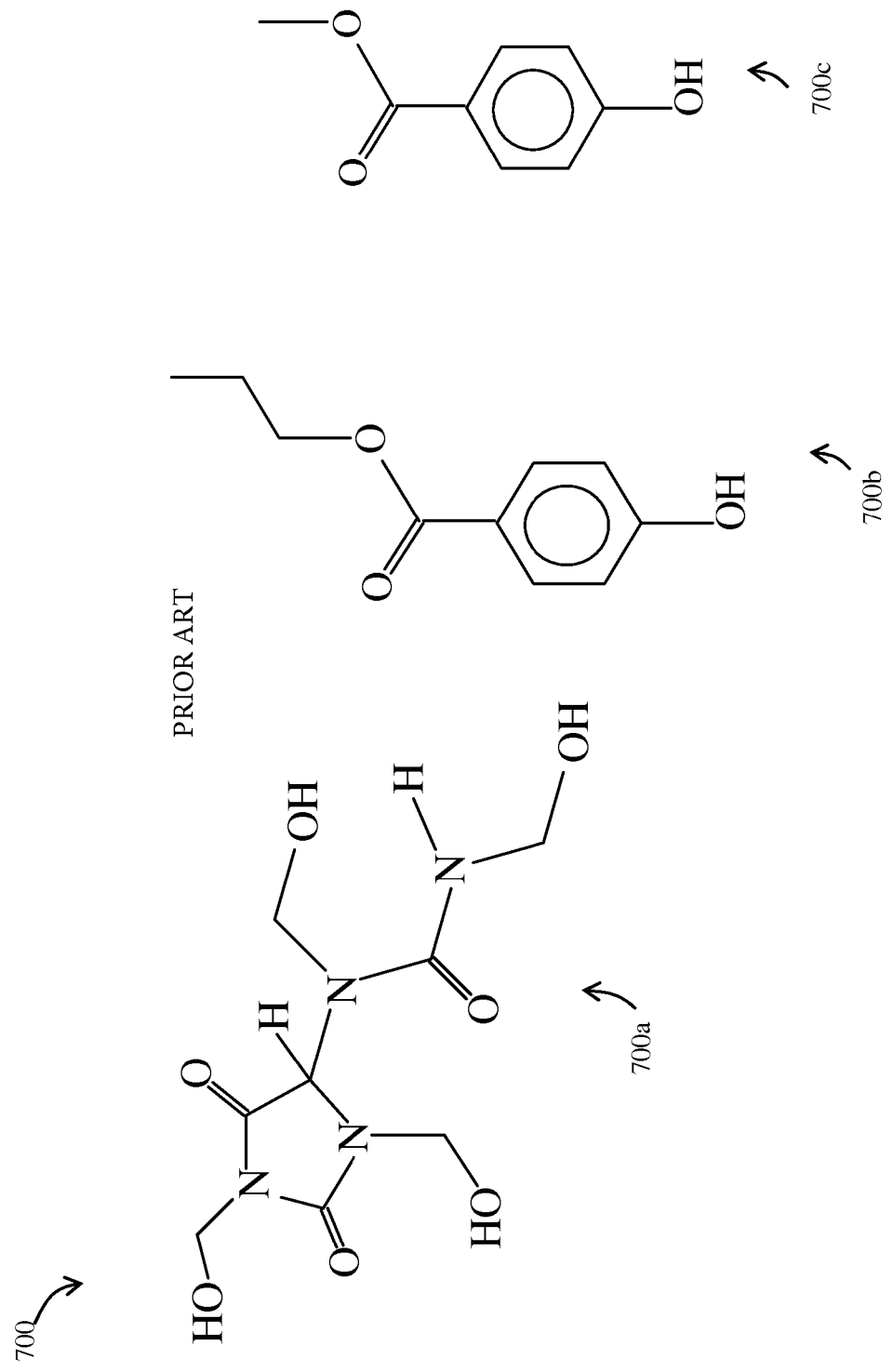
FIG. 7 is a perspective view of the molecular structure of Parabens mixture.

"Parabens mixture" is used to preserve products and prohibit the growth of fungi and bacteria to extend the shelf life of a product. It further comprises of propylparaben, methaylparaben, and diazolidinyl urea as three-broad spectrum preservatives in the formulation. The ingredients of the parabens mixture 700 (percent weight its total composition) include a formulation of: 3 percent of propylparaben 700b, 11 percent of methylparaben 700c and 30 percent diazolidinyl 700a; and at least 0.1 percent of ethylenediamine tetraacetic acid 800. Propylparaben may function in the formulation as a preserving agent while methaylparaben and diazolidinyl may function in the formulation as bacterial and fungi growth retardant each of which as represented by the structures shown in FIG. 7. Parabens mixture may not exceed 0.2 percent by weight of the total composition.

Figure 8:
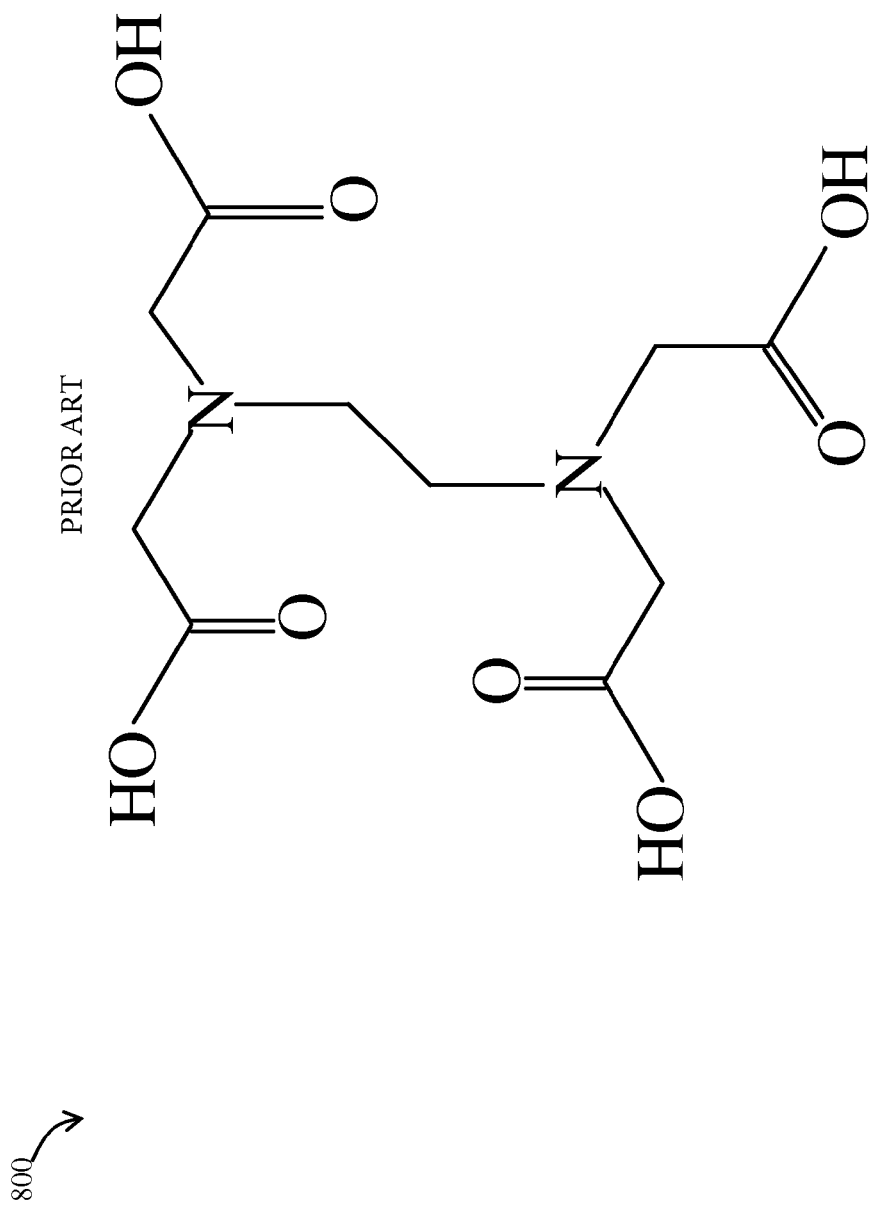
FIG. 8 is a perspective view of the molecular structure of Ethylenediamine tetraacetic acid.

"Ethylenediamine tetraacetic acid" meaning "EDTA" and its salts are crystalline powders used in cosmetics and personal care products and may function in the formulation to bind metal ions, prevent deterioration of topical clove essential oil delivery system, maintain clarity, protect fragrance compounds and prevent rancidity as represented by the structure shown in FIG. 8. EDTA may not exceed 0.1 percent by weight of the total composition.

"Aloe barbadensis leaf extract" means "aloe" and "aloe vera" has fungicidal, antimicrodial, and antiviral activity and has been effective in would healing and infection treatment in animals. Aloe derived ingredients enhance the appearance of dry or damaged skin by reducing flaking and restoring suppleness. Aloe in the composition may function as a skin conditioning agent to enhance the capacity of skin hydration. Aloe barbadensis leaf extract may not exceed 0.1 percent by weight of the total composition.

The gel for topical application of clove essential oil 100 with broad spectrum anti-inflammatory action provides a method of preparing an anti-inflammatory topical application of clove essential oil. In a first step 1101, the method includes first sprinkling acrylates/C10-30 alkyl crosspolymer 200 on the surface of the deionized water. As a next step 1102, the composition created in step 1101 is mixed at a low speed after the polymer is thoroughly wetted. In step 1103, isopropyl alcohol SDA is dissolved in the acrylates/C10-30 crosspolymer and deionized water and the same is mixed until uniform.

As a next step 1104, a set of ingredients are added one after the other to the composition of step 1103—the added ingredients include: glycerin, tocopherol acetate, clove essential oil, black pepper essential oil, aloe barbadensis leaf extract, and a parabens mixture comprising propylparaben, methylparaben and diazolidinyl urea. The composition is mixed until uniform.

As a next step 1105, triethanolamine 1000 is added to the composition created in step 1104 to neutralize the composition at pH 5.5. In step 1106, fragrance is added to the composition created in step 1105 and the composition is mixed until uniform.

While certain embodiments of the invention have been described, other embodiments may exist. Although the subject matter has been described in language specific to structural features, it is to be understood that the subject matter defined in the appended claims is not necessarily limited to the specific features or acts described above. Rather, the specific features and acts described above are disclosed as example forms of implementing the claims.

Furthermore, although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. It is intended that the appended claims cover any and all such applications, modifications, and embodiments within the scope of the present invention.

What is claimed is:

1. A gel for topical application, comprising of:
   about 30.0 percent by weight of deionized water;
   about 0.3 percent by weight of acrylates/C10-30 alkyl acrylate crosspolymer;
   about 0.1 by weight of glycerin;
   about 0.2 percent by weight of triethanolamine;
   about 0.1 percent by weight of tocopherol acetate;
   about 0.5 percent by weight of fragrance;
   about 5 percent by weight of clove essential oil;
   about 2 percent by weight of black pepper essential oil;
   about 61.4 percent by weight of isopropyl alcohol SDA;
   at least 0.1 percent by weight of aloe barbadensis leaf extract;
   about 0.2 percent by weight of a mixture, wherein said mixture comprises, by weight, about 3 percent by weight of propylparaben, 11 percent by weight of methylparaben and 30 percent by weight of diazolidinyl urea; and
   at least 0.1 percent by weight of ethylenediamine tetraacetic acid.

2. A method for preparing a gel, comprising the steps of:
   sprinkling acrylates/C10-30 alkyl crosspolymer on a surface of deionized water;
   mixing the acrylates/C10-30 alkyl crosspolymer and the deionized water;
   dissolving isopropyl alcohol SDA in the acrylates/C10-30 alkyl crosspolymer and mixing;
   adding the following ingredients:
   glycerin, tocopherol acetate, clove essential oil, black pepper essential oil, aloe barbadensis leaf extract, a mixture comprising propylparaben, methylparaben and diazolidinyl urea and mixing;
   adding triethanolamine and fragrance and mixing;
   wherein aforementioned ingredients are added in amounts sufficient to yield the following percentages of ingredients in said gel:
   about 30.0 percent by weight of deionized water;
   about 0.3 percent by weight of acrylates/C10-30 alkyl acrylate crosspolymer;
   about 0.1 percent of by weight of glycerin;
   about 0.2 percent by weight of triethanolamine;
   about 0.1 percent by weight of tocopherol acetate;
   about 0.5 percent by weight of fragrance;
   about 5 percent by weight of clove essential oil;
   about 2 percent by weight of black pepper essential oil;
   about 61.4 percent by weight of isopropyl alcohol SDA;
   at least 0.1 percent by weight of aloe barbadensis leaf extract;
   about 0.2 percent by weight of a mixture comprising about 3 percent by weight of propylparaben, 11 percent by weight of methylparaben and 30 percent by weight of diazolidinyl urea; and
   at least 0.1 percent by weight of ethylenediamine tetraacetic acid.

3. A method for treating topical inflammation, comprising the steps of:
   periodically applying said gel topically to a patient's skin, wherein the gel comprises:
   about 30.0 percent by weight of deionized water;
   about 0.3 percent by weight of acrylates/C10-30 alkyl acrylate crosspolymer;
   about 0.1 by weight of glycerin;
   about 0.2 percent by weight of triethanolamine;
   about 0.1 percent by weight of tocopherol acetate;
   about 0.5 percent by weight of fragrance;
   about 5 percent by weight of clove essential oil;
   about 2 percent by weight of black pepper essential oil;
   about 61.4 percent by weight of isopropyl alcohol SDA;
   at least 0.1 percent by weight of aloe barbadensis leaf extract;
   about 0.2 percent by weight of a mixture, wherein said mixture comprises, by weight, about 3 percent by weight of propylparaben, 11 percent by weight of methylparaben and 30 percent by weight of diazolidinyl urea; and
   at least 0.1 percent by weight of ethylenediamine tetraacetic acid.

* * * * *